United States Patent [19]

Rosencwaig

[11] Patent Number: 4,521,118
[45] Date of Patent: Jun. 4, 1985

[54] METHOD FOR DETECTION OF THERMAL WAVES WITH A LASER PROBE

[75] Inventor: Allan Rosencwaig, Danville, Calif.

[73] Assignee: Therma-Wave, Inc., Fremont, Calif.

[21] Appl. No.: 401,511

[22] Filed: Jul. 26, 1982

[51] Int. Cl.$^3$ .................... G01N 21/41; G01N 25/72
[52] U.S. Cl. .......................................... 374/5; 356/43; 356/376; 356/381; 374/55; 374/57
[58] Field of Search ................ 374/210, 117, 6, 7, 374/5; 73/606, 579, 643, 655; 356/345, 349, 371

[56] References Cited

U.S. PATENT DOCUMENTS

| | | | |
|---|---|---|---|
| 3,434,332 | 3/1969 | Maley | 374/7 |
| 3,539,262 | 11/1970 | Pryor | 356/349 X |
| 3,667,846 | 6/1972 | Nater et al. | 356/371 |
| 3,948,345 | 4/1976 | Rosencwaig | 73/579 |
| 3,978,713 | 9/1976 | Penny | 73/643 |
| 4,014,613 | 3/1977 | Sharpe, Jr. et al. | 374/55 X |
| 4,109,508 | 8/1978 | Dukuyama | 374/5 |
| 4,159,522 | 6/1979 | Zanonc | 356/345 X |
| 4,255,971 | 3/1983 | Rosencwaig | 73/606 X |
| 4,299,494 | 11/1981 | Badoz et al. | 374/45 |

FOREIGN PATENT DOCUMENTS 0800614 1/1981 U.S.S.R. .................................. 374/7

OTHER PUBLICATIONS

"Scanning Photo-Acoustic Microscopy (SPAM)", Y. H. Wong, Scanned Image Microscopy, Academic Press, London, 1980.

"The Mirage Effect in Photo Thermal Imaging", Fournier & Boccara, Scanned Image Microscopy, Academic Press, London, 1980.

"Photothermal Spectroscopy Using Optical Beam Probing: Mirage Effect", -Murphy and Aamodt, Journal of Applied Physics, vol. 51, No. 9, Sep. 1980.

"Photoacoustic Microscopy at Low Modulation Frequencies", Luukkala, Scanned Image Microscopy, Academic Press, N.Y., 1980.

"Non-Contact Optical Position Sensing Using Silicon Photodetectors", W. Light, United Detector Technology Brochure, 4/1982, 23 pages.

"Visualization of Surface Elastic Waves on Structural Materials", Alers et al., Ultrasonics-Jul. 1973, pp. 174–177.

"Photothermal Radiometry for Spatial Mapping of Spectral and Material Properties", Nordal and Kanstad, Scanned Image Microscopy, Academic Press, London, 1980.

"Photodisplacement Imaging", (Amer et al.), Photoacoustic Spectroscopy Meeting, Technical Digest: Paper THA6,1, Optical Society of America-1981.

"Oblique Incidence Reflection Acoustic Imaging", Yeack and Chodorow, J. Applied Physics, 9/1980, pp. 4637–4644.

Publication 0 039 457 (EP), "Acoustic Microscope", 13 pages, 4 Figs., Hitachi et al., 4/24/81.

*Primary Examiner*—Daniel M. Yasich
*Attorney, Agent, or Firm*—Limbach, Limbach & Sutton

[57] ABSTRACT

A method for measuring thermal waves in a sample is disclosed. More particularly, thermal waves, which may be used for imaging, are generated in a sample through local periodic heating as, for example, by impinging an intensity modulated beam of energy on the surface of the sample. A laser probe is focused on a portion of the heated area on the surface of the sample in a manner such that the beam is reflected from the surface. The angular displacement of the reflected beam, resulting from the local angular change in surface conditions of the sample due to the thermal waves are monitored. By this arrangement, the displacement of the reflected beam can be used to detect the thermal waves.

15 Claims, 2 Drawing Figures

METHOD FOR DETECTION OF THERMAL WAVES WITH A LASER PROBE

TECHNICAL FIELD

The subject invention relates to a new and improved method for detecting thermal waves generated in a sample. More particularly, a non-contact measurement technique is disclosed wherein the angular displacement of a reflected laser beam probe is monitored to detect the thermal waves in a sample.

BACKGROUND OF THE INVENTION

Recently, there has been considerable interest in developing analytical techniques which utilize thermal-wave microscopy. In thermal-wave microscopy, a periodic heat source is focused on the surface of a sample. The heat source is typically supplied by either an intensity modulated laser beam, or a stream of particles such as an electron beam. If the sample absorbs the incident energy at or near the sample surface, a periodic surface heating results which in turn generates thermal waves that propagate from the irradiated spot. These thermal waves have the same frequency as the beam modulation frequency. The wavelength of the thermal waves is determined both by the frequency of the beam and by the thermal parameters of the sample.

In a thermal-wave microscope, thermal features beneath the sample surface are detected and imaged by sensing the thermal waves that scatter and reflect from these features. Thermal features are those regions of an otherwise homogeneous material that exhibit variations relative to their surroundings in thermal conductivity, thermal expansion coefficient or volume specific heat. Variations in these thermal parameters can arise from changes in basic material composition or from the presence of mechanical defects such cracks, voids and delaminations. Variations in thermal parameters can also arise from changes in the crystalline order or structure or due to the presence of small concentrations of foreign ions or lattice defects in an otherwise perfect crystal. The thermal waves are highly damped such that they travel only one or two wavelengths before becoming too weak to detect. Nevertheless, a variety of methods have been developed capable of sensing and measuring the thermal waves generated in a sample.

One method of detection includes the sensing of acoustic waves which are generated by the thermal waves. More particularly, acoustic waves are generated because thermal waves induce stress-strain oscillations in the heated region of the sample. These elastic waves are true propagating waves and can be detected with conventional ultrasonic transducers. It is believed that this technique, called thermoacoustic microscopy, was first disclosed in applicant's prior U.S. Pat. No. 4,255,971, issued Mar. 17, 1981, which is incorporated herein by reference.

While detection of thermal waves through the measurement of acoustic signals is effective, particularly at high frequency, it has certain disadvantages. For example, it is a "contact" technique requiring the attachment of an ultrasonic transducer to a sample. The latter requirement is time consuming and may not be suitable for high volume production situations. In addition, the acoustic signals may be influenced by other elastic effects such as plate-mode resonances. The detection of plate-mode resonances can be highly desirable when the goal is to evaluate the quality of the bond between two materials. (See, Applicant's co-pending Application, U.S. Ser. No. 381,891 filed May 25, 1982 and now U.S. Pat. No. 4,484,820 ). However, in other measurement situations, the various elastic and acoustic effects will complicate the thermal-wave analysis.

Accordingly, other methods are known in the prior art for detecting thermal waves which do not require any contact with the sample. For example, thermal-wave imaging can be performed by monitoring the local periodic temperature at the surface of the sample. One way of measuring the periodic temperature variations is through gas-microphone photoacoustics. In this technique, a sample is placed inside a closed chamber containing air and a sensitive microphone. Periodic conduction of heat from the sample surface to the air in the chamber gives rise to periodic pressure changes in the chamber. The periodic pressure changes can be detected by the microphone. (See, "Scanning Photo-Acoustic Microscopy (SPAM)", Wong, Scanned Image Microscopy, Academic Press, London, 1980).

Another method for measuring the periodic temperature changes at the surface of a sample includes the monitoring of a laser which traverses a gas or liquid medium that is in contact with the heated spot on the sample surface. The laser beam will undergo periodic deflections because of the periodic heat flow from the sample to the adjacent medium. (See, "The Mirage Effect in Photothermal Imaging", Fournier and Boccara, Scanned Image Microscopy, Academic Press, London, 1980). A third technique for measuring oscillating surface temperatures utilizes an infra-red detector that senses the periodic infra-red emission from the heated spot on the surface of the sample. (See, "Photoacoustic Microscopy at Low Modulation Frequencies", Luukkala, Scanned Image Microscopy, Academic Press, London, 1980).

The above-discussed techniques for measuring the periodic variations in the surface temperature of a sample provide adequate sensitivity at low modulation frequencies, for example, less than 10 kHz. As in all imaging systems employing waves, the resolution which can be obtained in a thermal-wave imaging system is dependent upon the wavelength of the imaging waves. Therefore, to obtain resolution in the micron and submicron range, it is necessary to use thermal waves that have wavelengths in a comparable range. Thermal waves in the micron and submicron range require beam modulation frequencies in the megahertz range. However, as pointed out above, the latter surface temperature detection techniques do not have sufficient sensitivity to operate at megahertz frequencies thereby precluding the imaging of micron and submicron features in a sample. Accordingly, it would be desirable to provide a detection system which could provide the desired sensitivity.

Recently, a measurement technique has been disclosed wherein local surface temperature fluctuations are measured using a laser interferometry system. This system depends upon the fact that the local temperature oscillations induced in a sample give rise to local vertical surface displacements caused by the expansion and contraction of the sample surface. A suitably designed laser interferometer could potentially detect surface temperature fluctuations at frequencies greater than 10 kHz. (See, "Photo Displacement Imaging", Ameri et al., Photoacoustics Spectroscopy Meeting, Technical Digest, paper THA6-1, Optical Society of America, 1981). However, it appears that even the disclosed interferometer system is not sufficiently sensitive to permit the imaging of micron size features. In addition, the development of interferometer systems may be restricted due to ancillary effects, such as changes in surface reflectivity caused by temperature oscillations or noise introduced by mechanical vibrations.

Accordingly, it is an object of the subject invention to provide a new and improved method for detecting thermal waves generated in a sample.

It is another object of the subject invention to provide a new and improved method for detecting thermal waves utilizing a laser probe.

It is a further object of the subject invention to provide a new and improved method for detecting thermal waves which is operative at frequencies in the megahertz range for imaging micron and submicron features.

It is still another object of the subject invention to provide a new and improved method for detecting thermal waves which does not require the attachment of an ultrasonic transducer in contact with the sample.

It is still a further object of the subject invention to provide a new and improved method for measuring thermal waves which is free from any elastic or acoustic effects present in thermoacoustic measurements.

DISCLOSURE OF THE INVENTION

In accordance with these and many other objects, the subject invention provides for a new and improved method for detecting thermal waves generated in a sample. The thermal waves are generated by periodically heating a localized spot on the surface of a sample. The periodic heating can be accomplished by any suitable means such as an intensity modulated laser or an electron beam. The thermal waves are detected by focusing a beam of energy, such as a laser, on a portion of the heated area on the surface of the sample in a manner such that the beam is reflected from the surface. The angular displacement of the reflected beam is then monitored. The displacement of the beam results from the local angular change in the surface of the sample due to the generation of thermal waves. Thus, the displacement of the beam can be used to detect the thermal waves in the sample. In the preferred embodiment, the angular displacement of the beam is measured utilizing photodetector devices such as a split detector or a quadrant detector.

Further objects and advantages of the subject invention will become apparent from the following detailed description, taken in conjunction with the drawings in which:

DETAILED DESCRIPTION OF THE INVENTION

Figure 1:
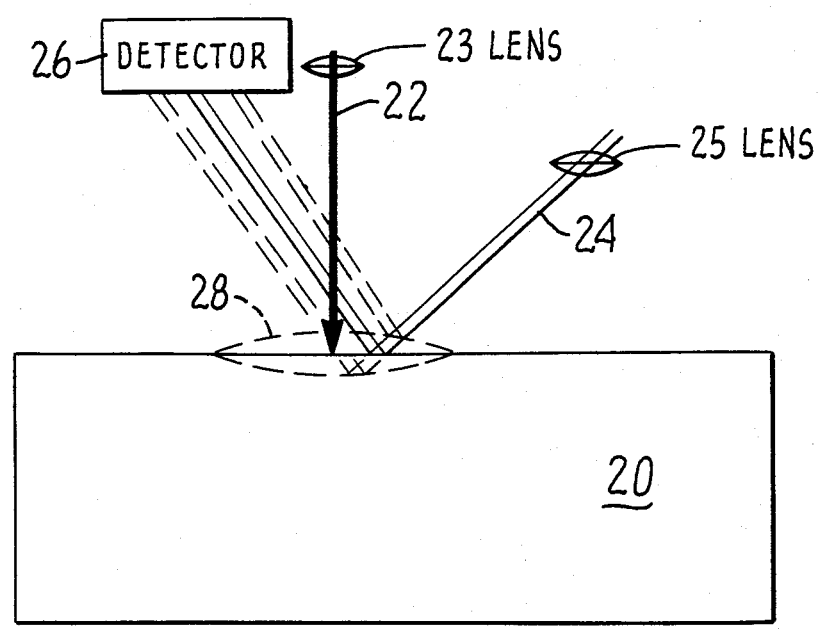
FIG. 1 is a simplified drawing illustrating one arrangement for performing the method for detecting thermal waves of the subject invention.
Figure 2:
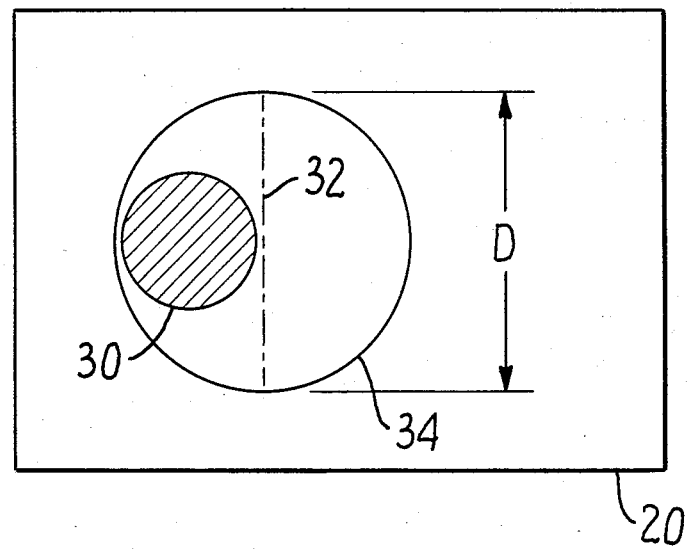
FIG. 2 is a simplified drawing illustrating the relationship between the heated area on the sample surface and the spot size of the laser probe.

Referring to FIGS. 1 and 2, the method of the subject invention will be more particularly described. Thermal waves can be generated by focusing a periodic heat source on the surface of the sample. One way of generating the periodic heating is by using an intensity modulated beam of electromagnetic radiation. Typically, the radiation will be supplied by a laser, but also can be generated from an incoherent light source. Various wavelengths such as X-rays, gamma rays, infra-red, ultra-violet, visible light, microwaves or radio frequencies can be used. Thermal waves can also be generated through the thermal excitations arising from the interaction of the sample with an intensity modulated stream of particles, such as a beam of electrons, protons, neutrons, ions or molecules. Another method for generating thermal waves includes passing a modulated electrical current through a sample to produce localized periodic heating. It is intended that the scope of the subject invention include any of the above heating modes.

Irradiation of the sample 20 at a spot on the surface of the sample with an intensity modulated beam of energy 22 gives rise to thermal waves. Where the heating beam is defined by a laser, a suitable optical lens system 23 is used for focusing the beam on the surface of the sample. The thermal waves radiate away from the irradiated spot and scatter and reflect from the surface and subsurface thermal features thereby making these features visible for imaging. A detailed discussion of thermal wave imaging can be found in appliant's co-pending U.S. patent application Ser. No. 389,623 filed June 18, 1982. The latter application describes various thermal imaging techniques including procedures for measuring thin film thicknesses and developing depth profiles of impurities and defects in a sample.

In order to carry out the latter and other imaging techniques, a suitable method must be developed for monitoring the thermal wave activity in a sample. The subject method is based on the fact that thermal waves generated in a sample result in local surface angular displacements or tilts. The movement or tilt of the sample surface is indicated by the dotted lines 28 in FIG. 1. These angular displacements are detected by focusing a beam of energy 24, in a manner to overlap a portion of the heated area on the surface of the sample 20. Energy beam 24 is perferably a laser probe, however any beam which exhibits specular reflection, that is, reflection off the front surface of the sample, in accordance with Snell's Law, is suitable. Thus, non-coherent light or even a particle beam could be utilized. However, a laser probe is preferred because the collimated beam is more accurate for measurement purposes. Where energy beam 24 is a laser probe, a suitable optical lens system 25 is provided for proper focusing.

After the beam reflects off the surface of the sample 20, it is monitored by a detector 26. As can be appreciated, due to the angular surface displacements of the sample in the area of the heated spot, the reflective path of the beam will oscillate. More particularly, as the angle of the surface of the sample fluctuates relative to the incoming beam 24, the beam will undergo periodic deflections. The amplitude and frequency of the deflections correspond with the amplitude and frequency of the thermal waves generated in the sample.

A variety of detectors are available in the prior art suitable for sensing the deflections of the laser probe. In the preferred embodiment, a form of split detector is utilized. A split detector consists of a photodetector having two sensing elements located side by side, separated by a divider only a few microns thick. Each sensing element generates an electrical signal based on the intensity of the light reaching that sector. By comparing the output of the two sensing elements, variations due to the deflection of the beam can be determined. The advantage of using a split detector is that any extraneous parameters, such as, for example, reflectivity changes in the sample, will effect both sides of the detector equally. Accordingly, a comparison of the output of both sensing elements will result in an elimination of any spurious parameters beyond the effects of beam deflection. This type of detector is also advantageous in that it tends to cancel any noise effects from the beam itself.

Another suitable detector which is available is a so-called "quadrant" detector. A quadrant detector includes plurality of sensing elements arranged in quadrant format. For example, a circular detector can be divided into four pie-shaped elements. A quadrant detector can provide even more detailed information as to the deflection angles of the beam. An explanation and illustrations of bicell and quadrant detectors can be found in "Non-Contact Optical Position Sensing Using Silicon Photodetectors," by William Light in the United Detector Technology publication dated April, 1982.

As mentioned above, the beam 24 is focused on a portion of the heated area on the surface of the sample. As can be appreciated, if the size of the probe spot 30 were to coincide with the entire heated area, the effects of the angular changes would tend to cancel out, thereby producing inaccurate information.

Referring to FIG. 2, the optimum arrangement for monitoring the angular change in the surface of the sample is illustrated. More particularly, the probe spot 30 is located entirely to one side of the center line 32 of the heated area 34. By restricting the probe to only one half of the heated area 34, the complementary and cancelling displacement effects of the other side of the heated area are eliminated.

In the optimum arrangement, it is also preferable to restrict the probe spot 30 to fall within the boundary of the heated area 34. By this arrangement, the entire probe beam will be effected by the angular displacement of the surface of the sample. As can be appreciated, any portions of the probe spot 30 which extended beyond the heated area would exhibit no deflection. Accordingly, by maximizing the area of the probe which will exhibit deflection, the signals sensed by the monitor will be maximized and sensitivity will be enhanced.

In order to determine the size of the heated area or "heated diameter" D, various factors such as the thermal diffusion length of the thermal waves and the spot size of the modulated energy beam 22 must be considered. The "heated diameter" can be defined as equal to the $2 \cdot \sqrt{(\text{spot radius } r_o)^2 + (\text{thermal diffusion length})^2}$, where the spot radius $r_o$ is defined as the radius of the modulated energy beam.

The above formula indicates that in the limiting case where the diameter of the heated spot size is significantly larger than twice the thermal diffusion length, the heated diameter D will correspond rather closely to the diameter of the spot size. In this situation, the probe spot 30 is adjusted to equal one-half the heated spot size. However, where the heated spot size $r_o$ is very small, the size of the heated diameter D is more principally a function of the thermal diffusion length. Because thermal waves move out in all directions, the heated diameter D will be equal to twice the size of the thermal diffusion length. Therefore, in the latter limiting case, the probe spot 30 can be adjusted to equal one thermal diffusion length. Of course, many test situations will fall between the two limiting cases. Therefore the probe spot size is optimally adjusted to be equal to one-half the heated diameter D, as defined by the above-recited formula. Where a beam modulation frequency selected is so high that the thermal diffusion length is smaller than the optical wavelength of the probe, it will be necessary to have the diameter of the heated spot size greater than an optical wavelength to permit detection.

The subject detection method has excellent sensitivity and can detect displacements of less than $10^{-3}$ Angstroms, while permitting operation at frequencies in the megahertz range. The subject detection system, besides being sensitive and operable at high frequencies, is also advantageous in that it is a non-contact technique that does not interfere with the sample. In addition, the measured signals are free of any elastic or acoustic affects that tend to complicate thermal wave analyses. The latter result is achieved because, although acoustic signals are generated by the thermal waves, the accoustic signals are significantly smaller than the local thermal displacements and will not produce interferring signals.

In summary, there has been provided a new and improved method for measuring thermal waves in a sample. The thermal waves are generated by a periodic localized heating at a spot on the surface of the sample. The subject method includes focusing a laser probe on a portion of the heated area on the surface of the sample in a manner such that probe beam is reflected from the surface. Angular changes in the surface conditions of the sample, due to the thermal waves, cause the angular displacement of the reflected beam. By monitoring the displacement of the reflected beam, thermal waves can be detected.

While the subject invention has been described with reference to a preferred embodiment, it is to be understood that various other changes and modifications could be made therein, by one skilled in the art, without varying from the scope and spirit of the subject invention as defined by the appended claims.

I claim:

1. A method for detecting thermal waves in a sample, said thermal waves being generated in an area by a periodic localized heating at a spot on the surface of the sample, said thermal waves radiating outwardly from said spot, said method comprising the steps of:

focusing a probe beam of energy within a preselected portion of said area on the surface of the sample which is being periodically heated by the thermal waves, in a manner such that said beam is reflected from said surface; and monitoring the periodic angular displacement of the reflected probe beam, said periodic displacement resulting from the periodic local angular change in the surface conditions of the sample induced by the presence of thermal waves generated by said periodic localized heating, whereby the periodic displacement of the reflected probe beam can be used to detect the thermal waves.

2. A method as recited in claim 1 wherein said probe beam of energy is focused on one-half of the area which is being periodically heated.

3. The method as recited in claim 1 wherein said probe beam of energy which is reflected off said area on the surface of said sample is defined by electromagnetic radiation.

4. The method as recited in claim 3 wherein said electromagnetic radiation is defined by light.

5. The method as recited in claim 4 wherein said light is generated from a laser and is coherent.

6. The method as recited in claim 1 wherein said probe beam of energy which is reflected off said area on the surface of the sample is defined by a stream of particles.

7. The method as recited in claim 6 wherein the particles in said beam are electrons.

8. The method as recited in claim 1 wherein the angular displacement of the reflected beam is monitored utilizing a split detector.

9. The method as recited in claim 1 wherein the angular displacement of the reflected beam is monitored with a quadrant detector.

10. An apparatus for detecting thermal waves in a sample, said thermal waves being generated in an area by a periodic localized heating at a spot on the surface of the sample, said thermal waves radiating outwardly from said spot, said apparatus comprising:
   a probe beam of energy;
   means for focusing said probe beam within a preselected portion of said area on the surface of the sample which is being periodically heated by the thermal waves in a manner such that said probe beam is reflected from the surface; and
   means for monitoring the periodic angular displacement of the reflected probe beam, said periodic displacement resulting from the periodic local angular change in the surface conditions of the sample induced by the presence of thermal waves generated by said periodic localized heating, whereby the periodic displacement of the reflected probe beam can be used to detect the thermal waves.

11. An apparatus as recited in claim 10 wherein said means for focusing said probe beam functions to focus said probe beam on only one-half the area on the surface of the sample which is periodically heated.

12. A method for evaluating thermal features in a sample comprising:
   generating a periodic localized heating at a spot on the surface of the sample to produce thermal waves which radiate outwardly from said spot in an area on the sample surface;
   focusing a probe beam of energy within a preselected portion of said area on the surface of the sample which is being periodically heated by the thermal waves, in a manner such that said beam is reflected from said surface; and
   monitoring the periodic angular displacement of the reflected probe beam, said periodic displacement resulting from the periodic local angular change in the surface conditions of the sample induced by the presence of thermal waves generated by said periodic localized heating, whereby the periodic displacement of the reflected probe beam can be used to evaluate thermal features in a sample.

13. A method as recited in claim 12 wherein said probe beam of energy is focused on one-half of the area on the surface of the sample which is being periodically heated.

14. An apparatus for evaluating thermal features in a sample comprising:
   means for generating a periodic localized heating at a spot on the surface of the sample to produce thermal waves which radiate outwardly form said spot in an area on the sample surface;
   a probe beam of energy;
   means for focusing said probe beam within a preselected portion of said area in the surface of the sample which is being periodically heated by the thermal waves in a manner such that said probe beam is reflected from the surface;
   means for monitoring the periodic angular displacement of the reflected probe beam, said periodic displacement resulting from the periodic local angular change in the surface conditions of the sample induced by the presence of thermal waves generated by said periodic localized heating, whereby the periodic displacement of the reflected probe beam can be used to evaluate said thermal features in a sample.

15. An apparatus as recited in claim 14 wherein said means for focusing said probe beam functions to focus said probe beam on only one-half the area on the surface of the sample which is periodically heated.

* * * * *